United States Patent [19]

van der Meij et al.

[11] Patent Number: 5,442,120

[45] Date of Patent: Aug. 15, 1995

[54] PRODUCTION OF DOBUTAMINE COMPOUNDS

[75] Inventors: Paulus F. C. van der Meij; Paulus P. G. de Jong, both of Weesp, Netherlands

[73] Assignee: Duphar International Research B.V., Weesp, Netherlands

[21] Appl. No.: 224,877

[22] Filed: Apr. 8, 1994

[30] Foreign Application Priority Data

Apr. 13, 1993 [EP] European Pat. Off. ............ 93201071

[51] Int. Cl.$^6$ ............................................. C07C 213/00
[52] U.S. Cl. .................................... 564/375; 564/374; 564/381
[58] Field of Search .................... 564/374, 375, 381

[56] References Cited

U.S. PATENT DOCUMENTS

| 2,276,619 | 3/1942 | Kulz | 260/570.8 |
| 4,329,367 | 5/1982 | Francis | 564/161 X |

FOREIGN PATENT DOCUMENTS

| 1061738 | 4/1954 | France . |
| 58928 | 4/1941 | Netherlands . |
| 695341 | 8/1953 | United Kingdom . |
| 1392674 | 4/1975 | United Kingdom . |

Primary Examiner—Richard L. Raymond
Attorney, Agent, or Firm—Stevens, Davis, Miller & Mosher

[57] ABSTRACT

The invention relates to a process for the production of an acid addition salt of a dobutamine compound of the general formula

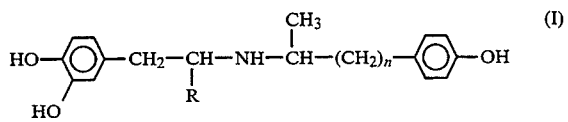

wherein R is a hydrogen atom or a methyl group, and n is 1 or 2, by reacting a mineral acid—addition salt of a dopamine compound of the general formula

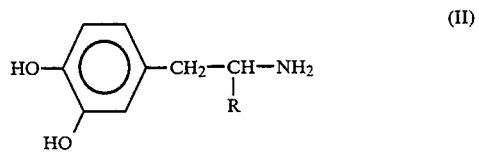

with a ketone of the general formula

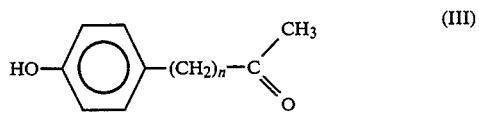

under the influence of a catalytic amount of a base, and in the presence of hydrogen and a hydrogenation catalyst, after which the pH of the reaction mixture is adjusted to approx. 6 at most and the product is isolated.

11 Claims, No Drawings

PRODUCTION OF DOBUTAMINE COMPOUNDS

The present invention relates to a process for the production of acid addition salts of dobutamine compounds.

N-[3-(4-hydroxyphenyl)-1-methylpropyl]-2-(3,4-dihydroxyphenyl)-ethylamine, generally known under its generic name dobutamine, is marketed as its HCl salt for treating cardiac insufficiency. This product, as well as its preparation process and pharmacotherapeutic properties, is described in British patent specification 1,392,674. The preparation process is carried out by a reductive amination of 4-(4-methoxyphenyl)butan-2-one, viz. by reacting this ketone with homoveratrylamine under reducing conditions ($H_2$, Pd/C). After purification, the intermediate so obtained, viz. the trimethyl ether of dobutamine, is demethylated under the influence of 48% hydrobromic acid in glacial acetic acid, then converted to the corresponding HCl salt, and finally purified by recrystallization from 4N hydrochloric acid.

In a Japanese patent application, recently published under no. 04/013652, an improved method of demethylation is described, using highly concentrated hydrochloric acid instead of hydrobromic acid and thus avoiding the salt-conversion step. Another improvement, viz. in the purification of dobutamine. HCl, is described in DDR patent 0153365. The conversion of dobutamine. HCl to other dobutamine salts is the subject of the European patent applications, published under nos. 0187019 and 0280461.

DDR patent 0153366 relates to a method of preparing dobutamine by subjecting 4-(4-methoxyphenyl)butan-2-one together with dopamine. HCl, i.e. 2-(3,4-dihydroxyphenyl)ethylamine. HCl, to a reductive amination ($H_2$, Pd/C). The monomethyl ether of dobutamine, obtained as its HCl salt, is then converted with a solution of ammonia in methanol into the soluble free base and, after separation of the catalyst, reconverted to its HCl salt. The subsequent demethylation and purification is carried out as described above for the trimethyl ether of dobutamine, producing the desired dobutamine salt. The advantage of this method, compared to the production process described in the above British patent specification, should reside in the combination of moderate reaction conditions and a substantially impurity-free product.

The improvements described in the above, more recent patent publications, reveal already the problems encountered by performing the preparation process as described in G.B. 1,392,674. To avoid the use of highly oxidation-sensitive phenolic compounds, this process starts from phenyl methyl ethers, and contains three separate reaction steps in addition to the final purification, viz. (i) reductive amination, (ii) demethylation, and (iii) conversion of the HBr salt into the desired HCl salt.

The above more recent patent publications, however, did not come up to the expectations raised in said publications. The demethylation with HCl instead of HBr, as described in the above Japanese patent application, requires even a reflux period (in highly concentrated hydrochloric acid) of 64 hours (HBr: 4 hours) to afford complete demethylation. The avoidance of reaction step (iii) does not compensate for this disadvantage. The improvement in the purification of the final product, reported in DDR patent 0153365, is marginal at most. The process described in DDR patent 0153366 does not result in any reduction in the number of reaction steps, although the reductive amination could be performed under a substantially lower hydrogen pressure. Further the considerable molar excess (50%) of the ketone reactant as compared with the other reactant, viz. dopamine. HCl, resulting in a large quantity of material to be discarded, is a serious disadvantage. Also the demethylation step, using 48% HBr, aggressive upon use and detrimental to the environment, could not be improved. Finally the overall yield is not satisfactory, viz. only 60%.

It is the objective of the present invention to provide a process for the production of a dobutamine compound, which process should meet the following requirements: (a) applying readily available starting materials, (b) using moderate reaction conditions, (c) producing the desired product in a substantially reduced number of reaction steps, (d) applying less aggressive reagents, and (e) using the reactants in such molar ratios that the environment is less burdened.

The term dobutamine compounds used throughout the specification and claims encompasses dobutamine and homologous compounds.

This objective can be achieved by a process for the production of an acid addition salt of a dobutamine compound of the general formula

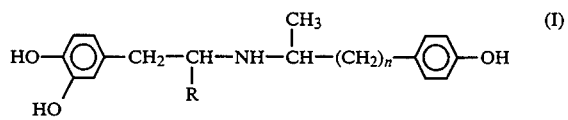

wherein R is a hydrogen atom or a methyl group, and m is 1 or 2,
which process is characterized according to the present invention, in that a mineral acid—addition salt of a dopamine compound of the general formula

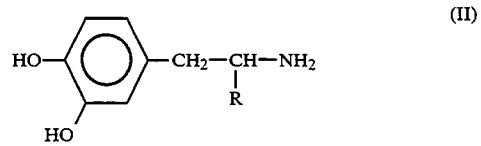

is reacted with a ketone of the general formula

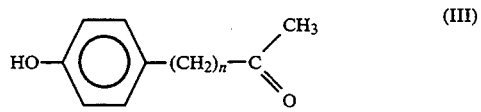

under the influence of a catalytic amount of a base, and in the presence of hydrogen and a hydrogenation catalyst, after which the pH of the reaction mixture is adjusted to approx. 6 at most and the product is isolated.

The starting materials II and III for the above reductive amination reaction are readily available. Instead of the original three separate reaction steps a one-step synthesis is sufficient to produce the desired product. The use of a base in a catalytic quantity allows the application of non-etherified phenolic starting compounds of which the dopamine compound is applied as its acid addition salt. In this manner a laborious demethylation step, moreover forming an environmental burden, is avoided. Adjustment of the pH of the reaction mixture, after the reaction is complete, to approximately 6 at most, reduces the chance of oxidative by-products. Moderate reaction conditions can be used to produce the desired final product in a high yield and in a condition which allows a relatively simple and easy purification. Considerably less excess of the ketone reactant III has appeared to be sufficient to afford a complete reaction.

If the above adjustment of the pH has to be accomplished by adding a certain amount of an acid, preferably the same mineral acid is used as present in the addition salt of the starting dopamine compound II. In this manner the formation of mixed acid addition salts of the dobutamine compound, produced according to the invention, is avoided. A suitable mineral acid for this purpose is hydrochloric acid.

As an additional aspect of the present invention it has been found, that the reductive amination reaction of the invention proceeds highly selectively in the presence of platina on a suitable carrier, preferably platina on active carbon. Surprisingly it has been found, that by using platina as a catalyst, the desired dobutamine compound (as its acid addition salt) is produced without substantial formation of undesirable by-products. An amount of approximately 1% of said Pt/C catalyst is generally sufficient for the reaction, although the use of somewhat greater quantities is not detrimental. The catalyst can easily be recovered from the reaction mixture, e.g. by filtration. The use of palladium as a catalyst for the reductive amination, as described in the above publications, has certain disadvantages compared with the use of platina, the preferred catalyst for this reaction. It has appeared, that a palladium catalyst has to be used in considerably greater quantities, in the order of approximately 20% calculated on the starting materials, to afford the desired reductive amination; this is in conformity with what is disclosed in the above-mentioned British patent 1,392,674 and DDR patent 0153366. In the presence of a palladium catalyst the reductive amination reaction requires considerably longer reaction times and higher temperatures (approx. 50° C.) to reach complete conversion. Under such hydrogenation conditions, however, the formation of by-products on an undesirable level is observed.

The reaction of the present invention proceeds under the influence of a catalytic amount of a base. Suitable bases are alkali metal hydroxides, such as sodium hydroxide and potassium hydroxide, and amines, such as triethylamine and triethanolamine. The amount of the base to be used in the process of the invention is not very critical, although at most a less than equimolar quantity, calculated on the starting compounds II and III, is required. Addition of said base in a molar equivalent ranging from approx. 0.01 to approx. 0.8, calculated on the starting compounds, is appropriate to catalyse the desired reaction efficiently; generally an approximately 0.1 molar equivalent is sufficient.

As mentioned above, moderate reaction conditions are suitable to accomplish the desired reductive amination reaction of the invention. It will be obvious, that oxidizing conditions during the reaction and the work-up procedure should be avoided; a reduction in a hydrogen atmosphere is, of course, a good environment to exclude oxidative side-reactions. It has been observed, that the reaction proceeds effectively at about ambient temperature and in a hydrogen atmosphere having a pressure of approximately 1 bar. Methanol is a suitable solvent for the reductive amination reaction, but also other solvents such as ethanol can be used. Under such conditions the desired reaction is complete in about 4 hours, producing the final dobutamine compound in the form of its acid addition salt in a high yield and with a high selectivity.

As mentioned hereinbefore, the final product is produced in a condition which allows its relatively simple and easy purification. In the known preparation process the obtained dobutamine.HCl is purified by a recrystallization from boiling hydrochloric acid. This requires a corrosion-resistant crystallization device and involves waste material which is detrimental to the environment. It has been found, that the final product of the process of the present invention can conveniently be purified by a crystallization from an organic solvent or solvent mixture and/or a (re)crystallization from water, if desired in the presence of an antioxidant. In this manner the desired addition salt of the dobutamine compound is obtained in a pharmaceutical quality. Preferably the final product of the process of the invention is crystallized from an organic solvent or solvent mixture and then recrystallized from water. A suitable organic solvent mixture for the crystallization is, for example, a mixture of 100% ethanol and toluene in a volume ratio of approx. 2:1.

The invention will now be described in greater detail with reference to the following specific example.

EXAMPLE

Preparation of dobutamine-hydrochloride [(±)-N-[3-(4-hydroxyphenyl)-1-methylpropyl]-2-(3,4-dihydroxyphenyl)ethylamine].

Reaction equation:

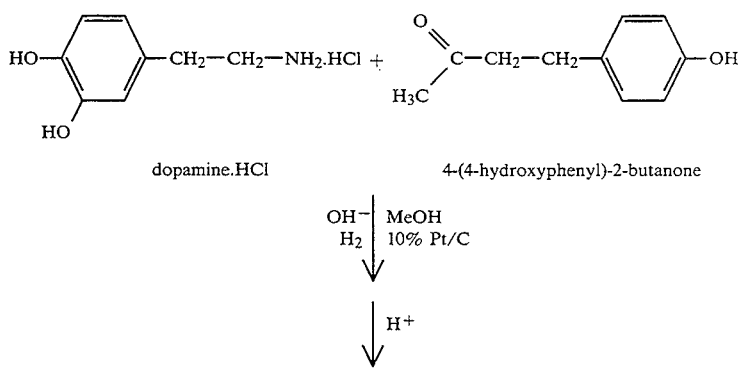

-continued

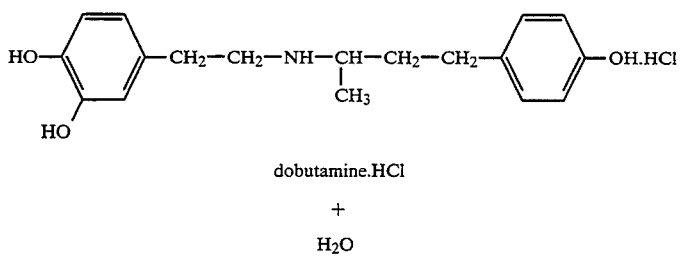

dobutamine.HCl

+

H₂O

The following reagents are combined under nitrogen:
- 189.6 g dopamine. HCl (1 mole),
- 189.6 g 4-(4-hydroxyphenyl)-2-butanone (1.15 mole),
- 4.75 g 10% Pt/C paste (corresp. with 1.9 g dry Pt/C),
- 5.2 ml 50% aqueous sodium hydroxide solution (0.1 mole), and
- 1140 ml methanol.

The nitrogen atmosphere is replaced by a hydrogen atmosphere, and the reaction mixture is stirred effectively at 15°–25° C. and 1.0–1.1 bar till the hydrogen consumption has stopped (after approx. 4 hours). After substituting a nitrogen atmosphere for the hydrogen atmosphere, 9 ml 36% hydrochloric acid is added; the pH of the reaction mixture is now below 6. The reaction mixture is then filtered to recover the platina catalyst. If desired, the addition of hydrochloric acid may be postponed till after the filtration. The methanol is now evaporated under diminished pressure (till approx. 100 mbar) and at an external temperature of 100° C. at most. The residue is taken up into 380 ml 100% ethanol of 70° C.; to this solution 300 ml toluene is added. The reaction mixture is now filtered to remove crystallized NaCl. After addition of 300 ml 100% ethanol, the reaction mixture is cooled to 15°–25° C. while stirring. After stirring for 1 hour at this temperature, the crystalline material is filtered off and washed twice with 400 ml acetone. After drying, the desired dobutamine. HCl is obtained in a yield of 321 g (93%); purity (HPLC): ≧98%.

If desired, the obtained dobutamine. HCl can be further purified by dissolving it in 963 ml demineralized water of 95° C. Sodium metabisulphite (Na₂S₂O₅) is added as an antioxidant in an amount of 1.6 g and the solution is cooled down to 50° C. After grafting, the aqueous solution is further cooled to 15°–25° C. while stirring. The mixture is stirred at the same temperature for another 8 hours at least. The purified dobutamine. HCl is filtered off and washed twice with 150 ml cold water. The product is dried under nitrogen, producing dobutamine. HCl with a purity of ≧99%.

We claim:

1. A process for the production of an acid addition salt of a dobutamine compound of the formula

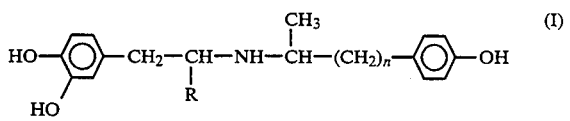

wherein R is a hydrogen atom or a methyl group, and n is 1 or 2, characterized in that a mineral acid—addition salt of a dopamine compound of the formula

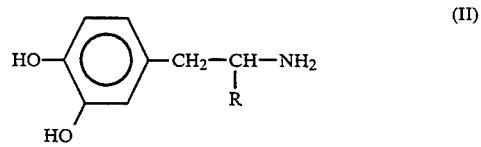

is reacted with a ketone of the formula

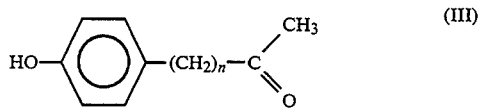

under the influence of a catalytic amount of a base, and in the presence of hydrogen and a hydrogenation catalyst, after which the pH of the reaction mixture is adjusted to about 6 at most and the product is isolated.

2. A process as claimed in claim 1, characterized in that the mineral acid is hydrochloric acid, and that the pH of the reaction mixture is adjusted with hydrochloric acid.

3. A process as claimed in claim 1, characterized in that the hydrogenation catalyst is platina on a suitable carrier.

4. A process as claimed in claim 1, characterized in that the base is an alkali metal hydroxide or an amine: and that said base is used in a molar equivalent ranging from about 0.01 to approx. 0.8, calculated on the starting compounds.

5. A process as claimed in claim 1, characterized in that the reaction is carried out at about ambient temperature and in a hydrogen atmosphere having a pressure of approximately 1 bar.

6. A process as claimed in claim 1, characterized in that the final product is purified by a crystallization from an organic solvent or solvent mixture and/or a (re)crystallization from water.

7. The process as claimed in claim 2, characterized in that the hydrogenation catalyst is platina on a carrier.

8. The process of claim 3 wherein the carrier is active carbon.

9. The process of claim 7 wherein the carrier is active carbon.

10. The process of claim 6 wherein the final product is purified in the presence of an anti-oxidant.

11. A process as claimed in claim 4, characterized in that the base is used in about a molar equivalent of 0.1, calculated on the starting compounds.

* * * * *